(12) United States Patent
Ullrich et al.

(10) Patent No.: US 10,161,884 B2
(45) Date of Patent: Dec. 25, 2018

(54) EXAMINING DEVICE AND METHOD FOR EXAMINING INNER WALLS OF A HOLLOW BODY

(71) Applicant: Sturm Maschinen- & Anlagenbau GmbH, Salching (DE)

(72) Inventors: Wolfgang Ullrich, Starnberg (DE); Florian Bader, Peissenberg (DE)

(73) Assignee: Sturm Maschinen- & Anlagenbau GmbH, Salching (DE)

( * ) Notice: Subject to any disclaimer, the term of this patent is extended or adjusted under 35 U.S.C. 154(b) by 84 days.

(21) Appl. No.: 15/316,117

(22) PCT Filed: Apr. 24, 2015

(86) PCT No.: PCT/EP2015/058906
§ 371 (c)(1),
(2) Date: Dec. 2, 2016

(87) PCT Pub. No.: WO2015/193010
PCT Pub. Date: Dec. 23, 2015

(65) Prior Publication Data
US 2017/0097306 A1 Apr. 6, 2017

(30) Foreign Application Priority Data
Jun. 18, 2014 (EP) .................................. 14172886

(51) Int. Cl.
*G01N 21/954* (2006.01)
*G01B 11/12* (2006.01)
(Continued)

(52) U.S. Cl.
CPC ............ *G01N 21/954* (2013.01); *G01B 5/003* (2013.01); *G01B 11/12* (2013.01); *G01N 21/251* (2013.01);
(Continued)

(58) Field of Classification Search
CPC ............... G01N 21/954; G01N 21/251; G01N 21/8806; G01B 11/12; G02B 23/2461;
(Continued)

(56) References Cited

FOREIGN PATENT DOCUMENTS

DE 197 46 662 A1 2/1999
DE 198 13 134 A1 10/1999
(Continued)

OTHER PUBLICATIONS

International Search Report issued in PCT/EP2015/058906, dated Aug. 20, 2015.
(Continued)

*Primary Examiner* — Thai Q Tran
*Assistant Examiner* — Christopher T Braniff
(74) *Attorney, Agent, or Firm* — Studebaker & Brackett PC

(57) ABSTRACT

An examining device for examining inner walls of a hollow body comprises: a rod-shaped camera device designed to record an image transversely with respect to its longitudinal axis; adjustment means for moving the camera device into and out of the hollow body; a grazing light illumination device for illuminating the inner walls and having emission directions that are transverse with respect to receiving directions, from which the camera device receives light from the illuminated inner walls, wherein an angle between the emission and receiving directions is between 45° and 135°; diameter determination means for determining an inner diameter of a cavity of the hollow body and comprising a light source and optical measuring means. Furthermore, a corresponding method for examining inner walls is described.

12 Claims, 3 Drawing Sheets

(51) Int. Cl.
  *G01N 21/25*   (2006.01)
  *G01N 21/88*   (2006.01)
  *G02B 23/24*   (2006.01)
  *H04N 5/232*   (2006.01)
  *H04N 5/225*   (2006.01)
  *G01B 5/00*    (2006.01)
  *G01J 3/46*    (2006.01)

(52) U.S. Cl.
  CPC ..... *G01N 21/8806* (2013.01); *G02B 23/2461* (2013.01); *G02B 23/2484* (2013.01); *H04N 5/23238* (2013.01); *G01J 3/46* (2013.01); *G01N 2201/061* (2013.01); *H04N 2005/2255* (2013.01)

(58) Field of Classification Search
  CPC ........... G02B 23/2484; H04N 5/23238; H04N 2005/2255
  See application file for complete search history.

(56) References Cited

FOREIGN PATENT DOCUMENTS

DE  10 2004 043 209 A1   3/2006
EP         1 797 813 A1   6/2007
WO           99/15853 A1   4/1999

OTHER PUBLICATIONS

Translation of International Preliminary Report on Patentability; PCT/EP2015/058906; dated Dec. 5, 2016.

EXAMINING DEVICE AND METHOD FOR EXAMINING INNER WALLS OF A HOLLOW BODY

The present invention relates according to claim 1 to an examining device for examining inner walls of a hollow body, in particular a cylinder bore in an engine block. The invention further relates according to claim 11 to a method for examining inner walls of a hollow body.

In the production of engine blocks, but also various other products, the wall properties of a cavity are of great importance. These walls can be provided with a special coating. For example, coatings are often applied, for example by wire-based or powder-based thermal spraying, to the running surfaces of cylinder bores in an engine block of an internal combustion engine or to running surfaces of working cylinders. By applying suitable coatings, in principle, numerous improvements can be achieved. These include: reducing the fuel consumption of internal combustion engines, use of lightweight construction materials, friction reduction, improvement in the heat removal, more compact structural forms and freedom from maintenance. To achieve such aims, the coatings must comply with surface parameters predefined within low tolerances. Cylinder defects, in particular irregularities of the cylinder inner walls, and material deposits are to be avoided. The reliable production and inspection of cylinder surfaces is thus of great importance.

DE 10 2004 043 209 A1 describes a method and a device for measuring the inner wall of a cavity, preferably a bore wall. For this, a CCD camera is provided which records an annular measurement beam reflected by the surface of the inner wall and thus measures a profile of the hollow body.

DE 198 13 134 A1 describes an inspection method for large receptacles which provides for images of the inner walls of the large receptacle to be recorded with a camera for inspection purposes.

To examine a cylinder bore in an engine block, in particular in a ship's engine, a measuring device that can be lowered into the cylinder bore is provided according to WO 99/15853, the measuring device, after being positioned, carrying out a plurality of individual measurements on the cylinder inner wall.

To measure a small cavity, EP 1 797 813 A1 provides an optical measuring device with confocal distance sensors. Point light sources are used to measure the inner wall of the cavity at selected points.

DE 197 46 662 A1 discloses a further measuring arrangement, which is also provided for measuring a bore. With a light beam deflected in a fan shape, an inner contour of the bore is detected with a detector device by means of light section methods.

In general the field of application of the invention is not limited to engine components, but instead includes all objects, wherein inner walls of a workpiece are to be inspected.

Known examining devices for examining inner walls of a hollow body and known methods for examining inner walls of a hollow body require a high degree of manual activities. Carrying out suitable measurements for the workpiece to be inspected and measurement evaluation place a relatively high knowledge requirement upon the user and are associated with great time resources. In addition the error rate is high.

Conventionally, a visual inspection of the inner walls can be provided, wherein a person checks the inner walls with the naked eye. However, slight roughness, still causing interference, cannot be detected in this way. The addition of simple examining devices, for example length and distance measuring elements, with which the user determines the diameter of a cylinder bore, is, nevertheless, associated with relatively great time resources. The requirements to be met with respect to the reliability of a control measurement in the case of small layer thicknesses, which are for example 300 µm, are particularly difficult to fulfil.

It can be regarded as an object of the invention to indicate an examining device and a method for examining inner walls of a hollow body, which can determine surface properties or defects on the inner walls reliably and within a short time, in particular in steps within a production process.

This object is achieved by the examining device having the features of claim 1 and by the method having the features of claim 11.

Advantageous variants of the method according to the invention and the examining device according to the invention are the subject matter of the dependent claims and are additionally explained in the following description, in particular in association with the figures.

An examining device according to the invention for examining inner walls of a hollow body, in particular a cylinder bore in an engine block, comprises at least:
a holding means for holding the hollow body,
a rod-shaped camera device which is designed to record an image transversely to a longitudinal axis of the rod-shaped camera device,
an adjustment means for moving the camera device into and out of the hollow body,
an illumination means for illuminating the inner walls of the hollow body,
electronic control and evaluation means which are designed to control the camera device for recording a panoramic image around the longitudinal axis of the rod-shaped camera device and to determine surface properties of the inner walls from image data recorded by the camera, and
a diameter determination means to determine an inner diameter of a cavity of the hollow body,
wherein the diameter determination means has a light source for emitting a light beam onto inner walls of the cavity and also optical measuring means (sensors) to detect light coming from the inner walls of the cavity, and
wherein the control and evaluation means are designed to determine the inner diameter of the cavity from measurement information of the diameter determination means.

The camera device and the diameter determination means can examine, simultaneously or one after the other, the same cavity or two different cavities of the hollow body. The aforementioned inner walls of a cavity, into which the camera device is moved, and the inner walls of the cavity, which are measured by the diameter determination means, can thus be either identical to each other or different from each other. In the latter case, the two cavities can be examined one after the other by both the camera device and also the diameter determination means.

Surface properties can include for example the roughness, the presence of scratches, flecks, the evenness of a coating, the colour and/or brightness of the inner walls.

The camera device can be designed to record a panoramic image through a single image recording. Alternatively or additionally, the control and evaluation means can be designed to control the recording of a plurality of images one after the other and then put these together to form a panoramic image. For this, it can be provided that the adjustment means rotates the camera device around the longitudinal axis between the different image recordings.

In a method according to the invention for examining inner walls of a hollow body, the examining device according to the invention is used, for the examination of the inner walls with the rod-shaped camera, so that at least one image is recorded with the rod-shaped camera device while the camera device has been moved by the adjustment means into the hollow body.

Significant advantages are achieved by the invention in that a workpiece can be checked with high precision and reliability without measures having to be carried out by a user.

A first core idea can be seen in facilitating a camera movement through a holding means for the hollow body and an adjustment means for the camera device, the camera movement being realised in a defined manner with respect to the hollow body to be examined. The positioning of the camera device and the diameter determination means, which is important for the measurement precision, can be carried out in an exact and reproducible manner.

In order to examine the inner walls within a short time and without excessive movements, the camera device may be capable of recording a panoramic image. A panoramic image can represent a 360° degrees image, which thus covers the whole area to be measured/examined in the circumferential direction of the inner walls.

The illumination means can comprise a reflected light device and/or a grazing light illumination device. As a reflected light device, its emitting optical system can be arranged beside a receiving optical system of the camera device. A main emission direction of the reflected light device can be substantially parallel to a main receiving direction of the camera device, for example at an angle of less than 20°.

A grazing light illumination device is on the other hand arranged so that emission directions of the grazing light illumination device, in which it illuminates inner walls during operation, are transverse relative to receiving directions, from which the camera device receives light from the illuminated inner walls. Slight unevenness or other irregularities of the inner walls can thus be easily detected. In this embodiment, emission directions of the illumination means are not substantially parallel to the receiving directions of the camera device. Instead, a grazing light illumination device is used, of which the emission directions are transverse relative to the receiving directions, from which the camera device receives light from the illuminated inner walls. A shadow cast in the case of height variations of the inner walls can be seen more effectively in this way.

The "emission directions" can be understood to mean the whole angle range, in which light is emitted from a respective point of the grazing light illumination device. Alternatively, the "emission directions" can be understood to be the angle range of the light emission, in which during measurement operation the emitted light actually also impinges on inner walls.

Unevenness can be detected particularly well if the angle between emission directions, with which a certain point of the inner walls is illuminated, and receiving directions, from which light coming from the same point is measured by the camera device, is close to 90°.

The angle between the emission directions of the grazing light illumination device and the receiving directions of the camera device can be between 45° and 135°, in particular between 60° and 120°, preferably between 75° and 105°.

Furthermore, for a large shadow being cast, the illumination direction relative to the longitudinal direction of the cavity under examination is crucial. These directions can preferably be almost parallel to each another. For example it can be provided that light emitted by the grazing light illumination device onto the inner walls impinges thereon at an angle which is smaller than 25°, preferably smaller than 15° or 10°.

The term "inner walls" can be understood to mean the inner shell surfaces of a cavity of a hollow body to be examined. The cavity can be open in principle at the two end faces lying opposite each another or merely at one of these faces.

The hollow body can be in principle any desired workpiece which has at least one recess or opening as a cavity. It can for example be an engine block, in which a plurality of cylinder bores are produced as cavities to be examined.

The holding means can in principle be designed as desired, provided that it can hold, i.e. support, the hollow body to be examined. At the same time it can also be adapted to transport the hollow body. The holding means can be designed so that a hollow body that is held assumes a defined position relative to other components of the examining device, for example relative to the camera device. Alternatively, however, the holding means can also be designed so that a hollow body can assume different positions on the holding means, as is the case for example with a conveyor belt as a holding means. In order to ensure, in this case also, that the camera device can be moved along a predefined movement path relative to the hollow body, position detection means can be present. These determine the position of the hollow body on the holding means. The adjustment means for moving the camera device are then controlled in dependence upon the detected position of the hollow body. The camera device itself can also be used as a position detection means or as part thereof.

Through the rod shape of the camera device, this can be easily introduced into differently shaped cavities. Being in a rod shape can be regarded in particular as a shape, of which the length is clearly greater than its cross-sectional dimensions, for example at least 4 times or at least 6 times as large. Not all means required for image recording have to be arranged within the rod shape. For example, by means of optical elements within the rod shape, an image can be produced on a camera chip which is located outside of the rod-shaped area.

The rod-shaped camera device comprises a light entry area, through which light for recording an image of the inner walls can enter into the camera device, the light entry area being, in particular exclusively, at the lower end of the rod-shaped camera device, i.e. at that end, with which it is first moved into the cavity. The light entry area can extend around the whole periphery (360°) of the rod shape for recording a panoramic image.

The camera device is moved by the adjustment means relative to the hollow body. It can thereby be provided that the camera device is also moved relative to the grazing light illumination device. This simplifies the construction of the grazing light illumination device, in particular with respect to size limitations, and facilitates a precise movement of the camera device. Alternatively, however, it can also be provided that the grazing light illumination device is rigidly coupled to the camera device and is thus adjusted together therewith. This provides, inter alia, the advantage that a consistent illumination of the area recorded by the camera device in each case is achieved for different positions of the camera device.

An adjustment process of the camera device through the adjustment means can generally be understood in that at least its field of vision, i.e. its detection arrange, is adjusted.

For example an outer mirror can be displaced while other components of the camera device remain fixed in place, for example a camera chip. For increased security in a harsher production environment, however, it may be preferred for the optical components to be accommodated in a rod-shaped housing, which can be moved by the adjustment means. An excess pressure can be built up in the rod-shaped housing and means can be provided for air flushing of front optical systems, through which light can enter or exit the housing. A protection against dust can hereby be improved. Also, all measurement and emission means, described here, of the examining device can be arranged in a climate-controlled measurement housing subjected to excess pressure.

The camera device can be designed so that it can record a panoramic image at one point in time. Alternatively, however, it can also be provided that the camera device is rotated by the adjustment means and thereby records a plurality of images one after the other, which are then put together by the electronic control and evaluation means to provide a single panoramic image.

The grazing light illumination device can be formed as a ring light which is arranged centred relative to the rod-shaped camera device. The ring area is thereby perpendicular to the longitudinal direction of the rod-shaped camera device. This improves the homogeneity of the illumination. For a design as a ring light, the grazing light illumination device can comprise a plurality of light sources, for example at least 4 or 8 light sources, which are arranged around a ring shape.

The grazing light illumination device can be arranged so that it is located outside of the hollow body when the camera device has been moved into the hollow body. When moving in the camera device, the grazing light illumination device can be moved as well or can remain still. Through the positioning outside of the hollow body, an illumination of the inner walls from a direction almost parallel to the longitudinal direction of the cavity can be achieved without fear of a collision with the hollow body.

The control and evaluation means can also be designed to determine a height profile or a roughness of the inner walls from the measurement data of the diameter determination means.

The diameter determination means can be formed in particular by at least one triangulation sensor. It can also comprise a plurality of triangulation sensors, for example at least four, which can be arranged in particular in a ring shape around the rod-shaped camera device.

A triangulation sensor can have, for example, separate emission and receiving optical systems, wherein light coming from an area illuminated via the emission optical system is guided by the receiving optical system, in dependence upon the distance of the area from the triangulation sensor, to different light-sensitive sensors or sensor areas.

The at least one triangulation sensor can be orientated so that it examines an area of the inner walls which is also simultaneously examined by the camera device.

Workpieces with a plurality of cavities are often examined. In such a case, the camera device and the diameter determination means can also simultaneously examine different cavities. Requirements upon a compact structural form are reduced in this way and the examination can nevertheless be realised in a short time. In this embodiment the camera device and the diameter determination means are preferably at an adjustable distance from each other which can be adapted to the distance of the cavities in the hollow body relative to each other.

If the diameter determination means is arranged relative to the camera device so that they can both be moved at the same time into different cavities, the diameter determination means can have associated drive means. The diameter determination means can be arranged so that it is moved in along the longitudinal axis of the cavity to be examined. This increases the precision of distance measurements relative to the inner walls.

The diameter determination means and the camera device can also be alternatively arranged, however, so that they simultaneously examine the same cavity.

It can be preferred for the diameter determination means to be rigidly coupled to the camera device. The two are thus adjusted in height via the adjustment means relative to the hollow body and can examine different height areas thereof one after the other.

The diameter determination means is preferably formed as a confocal sensor. In this, a joint optical element is provided for emitting light of the light source to the inner walls and for guiding light from the inner walls to the optical measurement means. In the case of the confocal sensor, an illuminated focal length coincides precisely with a measurement area which is sharply imaged.

The diameter determination means can comprise an optical waveguide which guides emitted light and/or light to be detected. The light source and the optical measurement means can thereby be positioned during measurement operation outside of the cavity under examination. The optical waveguide can extend parallel to the longitudinal axis of the rod-shaped camera device.

Drive means can be present for rotating the diameter determination means. Different areas of the inner walls can thereby be examined one after the other. The drive means can also be part of the adjustment means and, jointly with the diameter determination means, can also rotate the camera device.

In addition to the camera device, at least one colour sensor can be provided for determining the colour of inner walls of a hollow body. The electronic control and evaluation means can be adapted to compare colours, detected by the colour sensor, of inner walls with predefined values and to output a quality indication for the inner walls in dependence upon the comparison. The predefined values can be for example shades or tolerance values, by which colours measured/sensed one after the other may deviate from each other.

The electronic control and evaluation means can be adapted, on the basis of the recorded measurement values, i.e. the measurement data of the camera device and optionally the diameter determination means and optionally the colour sensor, to reach a decision on whether a hollow body under examination has a sufficient or insufficient quality. The examining device preferably also comprises a sorting device. This can be designed to further transport an examined hollow body optionally onto one of at least two different paths. A path is thereby selected in dependence upon whether a sufficient or insufficient quality of the hollow body has been determined.

The colour sensor can be rigidly coupled to the diameter determination means and thus, together therewith, be adjusted in height and rotated. The axis of rotation in this case is preferably central relative to the momentarily examined cavity. The diameter determination means can be arranged so that it is moved in a central or decentral manner into a hollow body that is held.

A colour differentiation of the colour sensor can usefully be better than that of the camera device.

Illumination means can be provided on the rod-shaped camera device that move therewith and can be arranged so that they illuminate the area of inner walls detected by the camera device. The illumination means can be part of the illuminating device. It can be provided that this and the grazing light illumination device are to be connected one after the other, wherein the camera device can record at least one image in each case. While the grazing light illumination device, due to its arrangement, highlights unevenness of the inner walls particularly well, the illumination means can preferably provide a particularly homogeneous illumination. In addition the grazing light illumination device and the illumination means can emit light in different wavelength ranges, whereby different information on the inner walls can be obtained. For homogeneous illumination, emission directions of the illumination means can be at a small angle relative to receiving directions of the camera device, for example at angles of less than 30° or less than 15°.

In order to further reduce the time required for the examination, the rod-shaped camera device can have a plurality of light entry areas, offset in its longitudinal direction, for recording a plurality of panoramic images offset in the longitudinal direction. For each of these light entry areas, an associated camera, i.e. a camera chip, can be present.

The examining device according to the invention can also have a plurality of camera devices and a plurality of diameter determination means. These can be moved by a shared adjustment means or at least simultaneously controlled. A plurality of cavities of a hollow body can be simultaneously examined in this way. This is useful for example for cylinders of an internal combustion engine. The plurality of camera devices and plurality of diameter determination means can be arranged at an adjustable distance relative to each other so that this distance can be adapted to the distance between the cavities to be examined.

In one variant of the method according to the invention, for the examination of different height areas of the inner walls with the rod-shaped camera device, a plurality of images are recorded one after the other while the camera device is being moved by the adjustment means into the hollow body and/or out of it. It is hereby possible in a short time to record the whole height area of the inner walls to be examined. If images are recorded either merely during inward movement or merely during outward movement, the inward or outward movement, during which no image recording takes place, can be carried out particularly quickly, i.e. in any case faster than the other of the inward or outward movement. Alternatively, images can be recorded both during the inward movement and also during the outward movement, whereby data redundancy and/or a greater measurement certainty can be achieved.

The adjustment means can be controlled so that it moves the camera device along a middle axis of a cavity of the hollow body into this hollow body. Through the movement along the middle axis, the subsequent data evaluation is simplified. For guiding along the middle axis, the camera device and the holding means for the hollow body can be arranged correspondingly relative to each other.

It can be advantageous if cavities with very different diameters can be precisely examined with the colour sensor and the diameter determination means. For this purpose, the drive means can be adapted to move the colour sensor and/or the diameter determination means transversely, in particular perpendicularly, relative to a longitudinal axis of the cavity. This adjustment can be realised automatically after a measurement of the distance from the colour sensor and/or from the diameter determination means to a wall of the cavity. The measurement of the distance can thereby be carried out with the diameter determination means. Advantageously, cavities of very different sizes can be examined in this way with one and the same examining device.

For a mechanically simple configuration it can be provided that the camera device and the colour sensor and/or the diameter determination means are moved one after the other into the same cavity to be examined. The camera device and the colour sensor or the diameter determination means can be arranged in a plane perpendicular to the longitudinal axis of the cavity offset relative to each, for example rotated by 180° around the longitudinal axis.

The properties of the invention described as additional device features are also to be regarded as variants of the method according to the invention, and vice versa.

Further advantages and features of the invention will be described below with reference to the attached schematic figures, in which.

The same components and those acting in the same way are generally identified in the figures by the same reference symbols.

Figure 1:
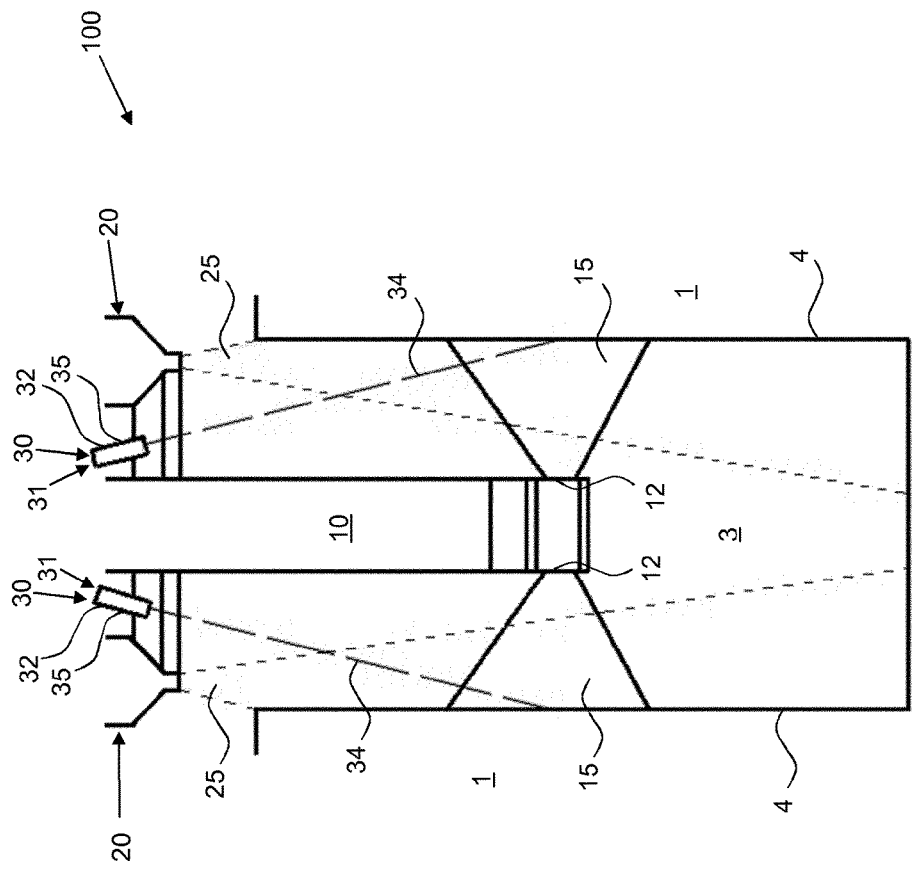
FIG. 1 shows a schematic illustration of a first exemplary embodiment of an examining device according to the invention.

FIG. 1 shows an exemplary embodiment of an examining device 100 according to the invention. This serves for the examination of inner walls 4 of a hollow body 1. For example, it can be used to examine cylinder running surfaces 4 of an engine block 1.

The hollow body 1 can have one or a plurality of cavities 3 which each have inner walls 4 to be examined. For example, coatings of the inner walls 4 may have to be examined.

The examining device 100 comprises, as principal components, a camera device 10, a grazing light illumination device 20 and a diameter determination means 30.

In addition the examining device 100 has a holding means (not shown here), with which the hollow body 1 is held at a desired and known position.

The camera device 10 has a rod-shaped housing. This is moved by an adjustment means (not shown) into the cavity 3. Via a light entry area 12 at the lower end of the rod-shaped housing, the camera device 10 can record an image of the environment. The field of vision 15 of the camera device 10 is transverse, in particular perpendicular to its longitudinal direction, which is defined by the rod shape. The field of vision preferably covers a 360° angle so that a panoramic image can be recorded.

The grazing light illumination device 20 serves for the illumination of the inner walls 4. The grazing light illumination device 20 is thereby arranged so that its emission directions 25 are transverse relative to receiving directions 15, i.e. relative to the area of vision 15, of the camera device 10. This can also be described as dark field illumination. Unevenness of the inner walls 4 thereby causes shadows to be cast relatively intensely which can then be determined by the camera device 10.

The grazing light illumination device 20 can provide an annular illumination which simultaneously illuminates a complete annular area of the inner walls 4.

The camera device 10 can record a plurality of images while it is being moved into and out of the cavity 3. Different height areas of the inner walls 4 can thereby be examined.

The images recorded are then evaluated by electronic control and evaluation means (not shown). With the aid of predefined criteria, the control and evaluation means reach a decision on whether the examined inner walls 4 have defects or not. Depending on this decision, the hollow body 1 can be further transported to different production stations.

As a substantial idea of the invention, the diameter of the cavity 3 is detected with a further optical measuring device. A coating thickness of the inner walls 4 or irregularities of a coating can also be concluded from the diameter. These measurements are realised with the diameter determination means 30 which has at least one light source 32 and optical measurement means 35.

In the example shown, this comprises a plurality of triangulation sensors 31 which are arranged so that they are directed, when the camera device 10 has been moved into the cavity 3, onto different points of the inner walls 4. The triangulation sensors 31 can be movable jointly with the camera device 10. Different height areas of the inner walls 4 can also be examined by the triangulation sensors 31.

Measurement results of the diameter determination means 30 are also considered by the control and evaluation means in order to reach the decision on whether the inner walls 4 have defects or not.

Figure 2:
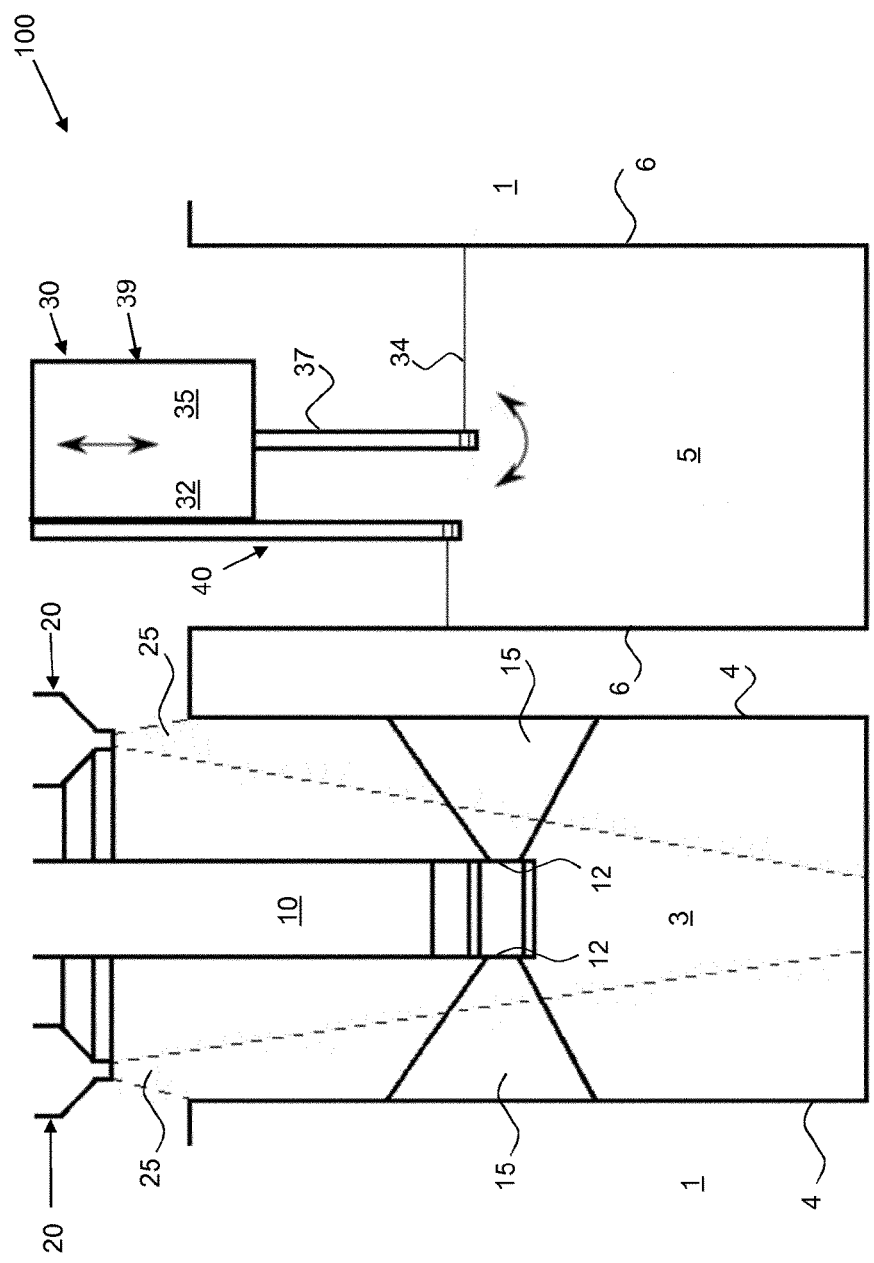
FIG. 2 shows a schematic illustration of a second exemplary embodiment of an examining device according to the invention and FIG. 3 shows a schematic illustration of a third exemplary embodiment of an examining device according to the invention.

In the embodiment of FIG. 2, a hollow body 1 is examined which has a plurality of cavities 3 and 5, which each have inner walls 4 and 6 to be examined. Here, the examining device 100 comprises in turn a camera device 10, a grazing light illumination device 20 and a diameter determination means 30.

The diameter determination means 30 is not formed here, however, by triangulation sensors. Instead, an optical distance measuring element/sensor 30 is used which is preferably configured as a confocal sensor 39. It comprises a waveguide 37, via which a measurement beam 34 is guided onto the inner walls 6. Light thrown back is also guided via the waveguide 37.

Furthermore a colour sensor 40 is present here, which performs a colour-sensitive measurement of the inner walls 6. The colour sensor 40 can also have a waveguide and can be coupled to the distance measuring element 30. The two can thereby be simultaneously moved into the cavity 5. In addition they can both be rotated together around the middle axis of the cavity 5, whereby the inner walls 6 can be scanned in the circumferential direction. The determination of the colour can help to detect defective points and/or layer thicknesses on the inner walls.

In the embodiment of FIG. 2, the diameter determination means 30 and the camera device 10 are simultaneously introduced into different cavities 3 and 5. These components do not interfere with each other even if their dimensions are fairly large. In addition, both can be moved along a middle axis of the respective cavity 5, whereby this facilitates the evaluation of the measurements.

Figure 3:
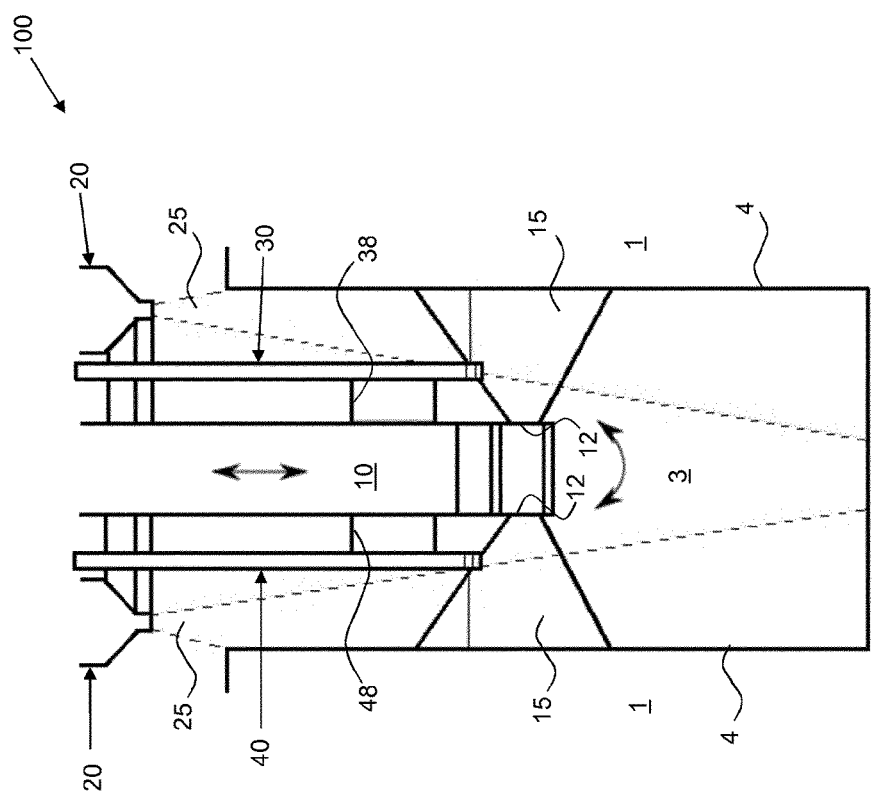

In the embodiment of FIG. 3, the examining device 100 comprises a camera device 10 and a grazing light illumination device 20, which can be designed as described for FIG. 1 or 2. The diameter determination means 30 and the colour sensor 40 are constructed here as in the embodiment of FIG. 2. However, they are coupled to the camera device 10 in the embodiment of FIG. 3. They are thus moved together with the camera device 10 into the same cavity 3. The diameter determination means 30 can be arranged outside of the field of vision 15 of the camera device 10, so that the measurements do not reciprocally interfere with each other. The grazing light illumination device 20 and the light source of the diameter determination means 30 can be controlled here one after the other, meaning that reciprocal interference is in turn avoided.

By rotating the measurement components 10, 30, 40 and optionally the grazing light illumination device 20, different circumferential portions of the inner walls 4 can be examined one after the other. Since, for the measurement components 30, 40, a rotation is necessary anyway, a design of the camera device 10 for recording a panoramic image is not necessarily required here. Instead, images of the camera device 10, recorded one after the other at the same height, can also be put together to form a panoramic image.

Through the examining device 100 according to the invention, hollow bodies can advantageously be examined particularly quickly and reliably. Defective hollow bodies can thus be filtered out without requiring steps to be taken by a user.

The invention claimed is:

1. An examining device for examining inner walls of a hollow body, the examining device comprising
   a holder for holding the hollow body,
   a rod-shaped camera device which is designed to record an image transversely with respect to a longitudinal axis of the rod-shaped camera device,
   an adjustment means for moving the camera device into and out of the hollow body,
   an illumination device, which is one or more light sources, for illuminating the inner walls of the hollow body,
   electronic control and evaluation unit which is designed to control the camera device for recording a panoramic image around the longitudinal axis of the rod-shaped camera device, and to determine from image data recorded by the camera device surface properties of the inner walls, and
   a diameter determination means for determining an inner diameter of a cavity of the hollow body, wherein
   the control and evaluation means are designed to determine the inner diameter of the cavity from measurement information of the diameter determination means,
   the diameter determination means has a light source which is provided in addition to the illumination device to emit a light beam onto inner walls of the cavity, and also has optical measuring means which are provided in addition to the camera device to detect light coming from the inner walls of the cavity,
   the illumination device comprises a grazing light illumination device which is arranged so that emission directions of the grazing light illumination device, in which it illuminates inner walls during operation, are transverse with respect to receiving directions, from which the camera device receives light from the illuminated inner walls, wherein an angle between the emission directions and the receiving directions is between 45° and 135° and
   the grazing light illumination device is arranged so that it is located outside of the hollow body when the camera device has been moved into the hollow body.

2. The examining device as defined in claim 1, wherein light emitted by the grazing light illumination device onto the inner walls is guided onto them at an angle which is smaller than 25°.

3. The examining device as defined in claim 1, wherein the rod-shaped camera device has a light entry area at its lower end, with which it is first moved into a cavity of the hollow body, wherein light can enter through the light entry area to record an image of the inner walls.

4. The examining device as defined in claim 1, wherein the illumination device is formed as a ring light which is arranged centered relative to the rod-shaped camera device.

5. The examining device as defined in claim 1, wherein the diameter determination means comprises at least one triangulation sensor.

6. The examining device as defined in claim 1, wherein the diameter determination means comprises a confocal sensor, wherein a shared optical element is provided for emitting light of the light source to the inner walls and for guiding light from the inner walls to the optical measurement means.

7. The examining device as defined in claim 1, wherein the diameter determination means is arranged relative to the camera device so that both can be moved at the same time into different cavities.

8. The examining device as defined in claim 1, wherein additionally a color sensor is provided for determining the color of inner walls of a hollow body, and the electronic control and evaluation unit is designed to compare detected colors of inner walls with predefined values and to output a quality indication for the inner walls in dependence upon the comparison.

9. The examining device as defined in claim 1, wherein the illumination device comprises light emitters on the rod-shaped camera device moving therewith, which are arranged so that they illuminate the area of inner walls detected by the camera device during operation.

10. The examining device as defined in claim 1, wherein the electronic control and evaluation unit is designed, on the basis of recorded measurement values, to reach a decision on whether an examined hollow body has sufficient or insufficient quality, and a sorting means is present which sorts the examined hollow body according to the criterion of whether a sufficient or insufficient quality of the hollow body has been determined.

11. A method for examining inner walls of a hollow body by the examining device as defined in claim 1, the method comprising:

examining the inner walls with the rod-shaped camera device, recording at least one image while the camera device has been moved by the adjustment means into the hollow body, locating the grazing light illumination device outside of the hollow body when the camera device has been moved into the hollow body, emitting a light beam with the light source onto inner walls of the cavity, and detecting light coming from the inner walls of the cavity with the optical measurement means.

12. The method as defined in claim 11, the method comprising:

moving the camera device along a middle axis of a cavity of the hollow body into the hollow body.

* * * * *